(12) United States Patent
Rossé

(10) Patent No.: US 9,078,672 B1
(45) Date of Patent: Jul. 14, 2015

(54) CARBON REAMER HANDLE

(75) Inventor: Yann Rossé, LaNeuveville (CH)

(73) Assignee: Greatbatch Medical S.A., Clarence, NY (US)

( * ) Notice: Subject to any disclaimer, the term of this patent is extended or adjusted under 35 U.S.C. 154(b) by 720 days.

(21) Appl. No.: 13/290,202

(22) Filed: Nov. 7, 2011

(51) Int. Cl.
*A61B 17/16* (2006.01)

(52) U.S. Cl.
CPC ......... *A61B 17/1631* (2013.01); *A61B 17/1664* (2013.01); *A61B 17/1666* (2013.01)

(58) Field of Classification Search
CPC ........... A61B 17/1631; A61B 17/1633; A61B 17/1666; A61B 17/1664; A61B 2017/320032; A61B 19/026
USPC ............. 606/87, 89, 79, 104, 180, 85, 88, 99, 606/62, 80–81, 91, 53
See application file for complete search history.

(56) References Cited

U.S. PATENT DOCUMENTS

| 5,462,548 | A | 10/1995 | Pappas et al. | |
|---|---|---|---|---|
| 7,008,430 | B2 | 3/2006 | Dong et al. | |
| 7,121,599 | B2 * | 10/2006 | Demar et al. | 294/60 |
| 7,513,899 | B2 | 4/2009 | Grim | |
| 7,611,515 | B2 | 11/2009 | Wolford et al. | |
| 7,682,363 | B2 * | 3/2010 | Burgi et al. | 606/91 |
| 8,475,460 | B1 * | 7/2013 | Roger et al. | 606/81 |
| 2005/0216020 | A1 | 9/2005 | Orton | |
| 2005/0261694 | A1 | 11/2005 | Orton et al. | |
| 2007/0073302 | A1 * | 3/2007 | Myers et al. | 606/80 |
| 2007/0293869 | A1 * | 12/2007 | Conte et al. | 606/91 |
| 2008/0058804 | A1 * | 3/2008 | Lechot et al. | 606/53 |
| 2008/0287952 | A1 | 11/2008 | Mcminn et al. | |
| 2009/0082772 | A1 | 3/2009 | Ferreira | |
| 2009/0192359 | A1 * | 7/2009 | Hale | 600/206 |
| 2010/0168749 | A1 | 7/2010 | Sidebotham et al. | |
| 2011/0082587 | A1 * | 4/2011 | Ziaei et al. | 700/260 |

FOREIGN PATENT DOCUMENTS

EP 2340787 7/2011
WO WO03092513 A1 * 11/2003

* cited by examiner

*Primary Examiner* — Eduardo C Robert
*Assistant Examiner* — Marcela I Shirsat
(74) *Attorney, Agent, or Firm* — Steven W. Winn; Michael F. Scalise

(57) ABSTRACT

A reamer for use in minimally invasive hip replacement surgical approaches is provided. The reamer spindle includes an offset elongate housing portion that extends from a proximal housing end portion a distal housing end portion. A handle assembly, preferably comprising a durable lightweight material such as carbon fiber that is removably connectable to the housing of the reamer spindle. A reamer head is removably connectable to the distal neck portion and has a surface configured to cut bone.

30 Claims, 16 Drawing Sheets

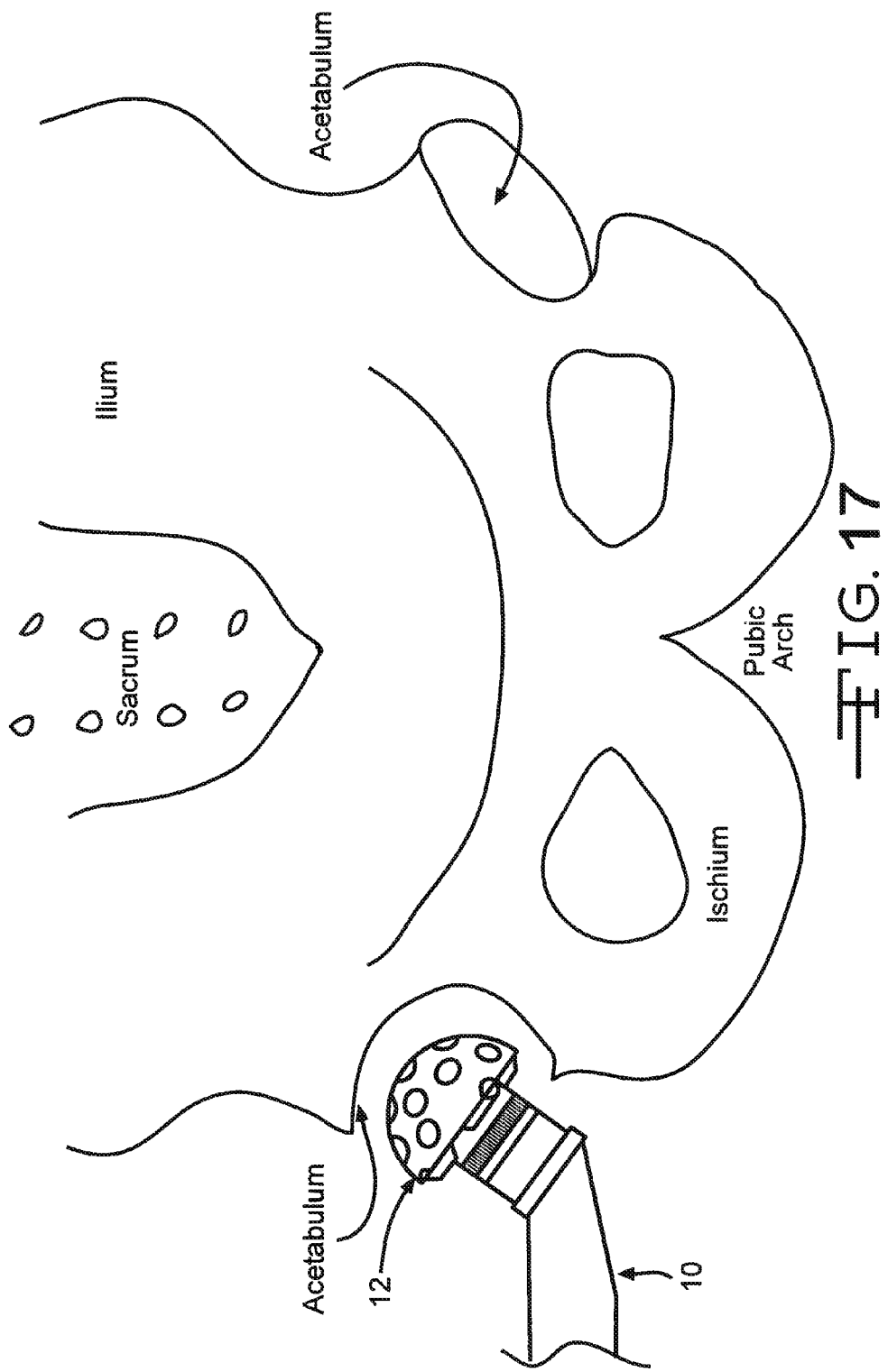

CARBON REAMER HANDLE

CROSS REFERENCE TO RELATED APPLICATIONS

This application claims priority to U.S. provisional application Ser. Nos. 61/410,418, filed on Nov. 5, 2010.

BACKGROUND OF THE INVENTION

Nearly 200,000 hip replacements are performed each year in the United States and the number is expected to continue to grow as the population ages. The usual reasons for hip replacement are osteoarthritis, rheumatoid arthritis and traumatic arthritis, all of which can cause pain and stiffness that limit mobility and the ability to perform daily living activities. Hip replacement surgery is usually performed when other measures (e.g., physical therapy, medications, and walking aids) are unable to overcome the chronic pain and disability associated with these conditions.

Various techniques are used by orthopedic surgeons to perform hip replacements. These include the following approaches: anterior, antero-lateral, anterior, posterior, and postero-lateral. The posterior and posteolateral approaches account for approximately 60% to 70% of hip replacement surgeries.

Traditional hip replacement surgery involves an open procedure and extensive surgical dissection. However, such procedures require a longer recovery period and rehabilitation time for the patient. The average hospital stay for open hip replacement procedures is 4-5 days, followed in most cases by extensive rehabilitation.

More recently, there has been considerable interest and research done in Minimally invasive Surgery (MIS), including the use of MIS procedures in connection with hip replacement surgery. In comparison with the traditional open surgical approach, MIS hip replacement surgeries involve fewer traumas to the muscles surrounding the hip joint. Specifically, fewer muscles that help to stabilize the hip joint are cut in MIS hip replacement surgeries, reducing the risk of dislocation of the hip surgery and speeding recovery. Patients spend less time in the hospital and return to normal life activities more quickly.

MIS approaches use smaller surgical fields, which require smaller instruments to perform the hip replacement procedures. One such instrument is a reamer spindle detachably connected to a surgical reamer. The surgical reamer is used to shape the bone of the acetabulum. However, reamer spindles have typically been straight with a handle in a fixed orientation. These prior art reamer spindles are not ideal for MIS approaches. The straight design and fixed handle orientation impedes the tool's ability to be used in small, tortuous spaces within the body, particularly of MIS procedures.

Accordingly, there is a need for an improved reamer spindle for use in MIS hip replacement surgical approaches. The present invention provides a reamer spindle with an offset reamer position and a handle that is able to be positioned in a multitude of orientations. These features of the reamer spindle of the present invention address previous shortcomings of previous reamer spindles, particularly for use in MIS procedures.

SUMMARY OF THE INVENTION

In accordance with one embodiment, a reamer for use in minimally invasive hip replacement surgical approaches is provided. The reamer spindle includes a housing with offset proximal and distal end portions. Specifically, the reamer spindle comprises an elongate housing portion that extends along a first longitudinal axis and a neck or distal portion that extends along a second longitudinal axis. A reamer head is removably connectable to the distal neck portion and has a surface configured to cut bone.

In accordance with another embodiment, the reamer spindle comprises a removable handle that is composed of a durable light weight material such as carbon fiber. The handle is designed such that it can be easily removed and positioned in multiple orientations about the proximal end portion of the spindle.

In accordance with still another embodiment, the elongate housing portion meets the distal neck portion at a rounded low profile surface configured to inhibit trauma to muscle tissue during use of the reamer spindle.

In accordance with yet another embodiment, the reamer can be driven by a source of rotational power, which may be an electric source. The housing is configured to enclose a rotatable shaft connectable to the reamer with the proximal end of the shaft being removably connectable to the source of rotational power. The housing may be composed of a polymer such as a durable lightweight carbon fiber material, a metal (e.g., stainless steel), super alloy or composite casing.

In accordance with another embodiment, the reamer spindle is configured in a way that it can be sterilized between uses.

BRIEF DESCRIPTION OF THE DRAWINGS

FIG. 17 is a schematic view of the orientation of the reamer spindle 10 during use in a minimally invasive hip replacement surgery.

DETAILED DESCRIPTION OF THE PREFERRED EMBODIMENTS

Figure 1:
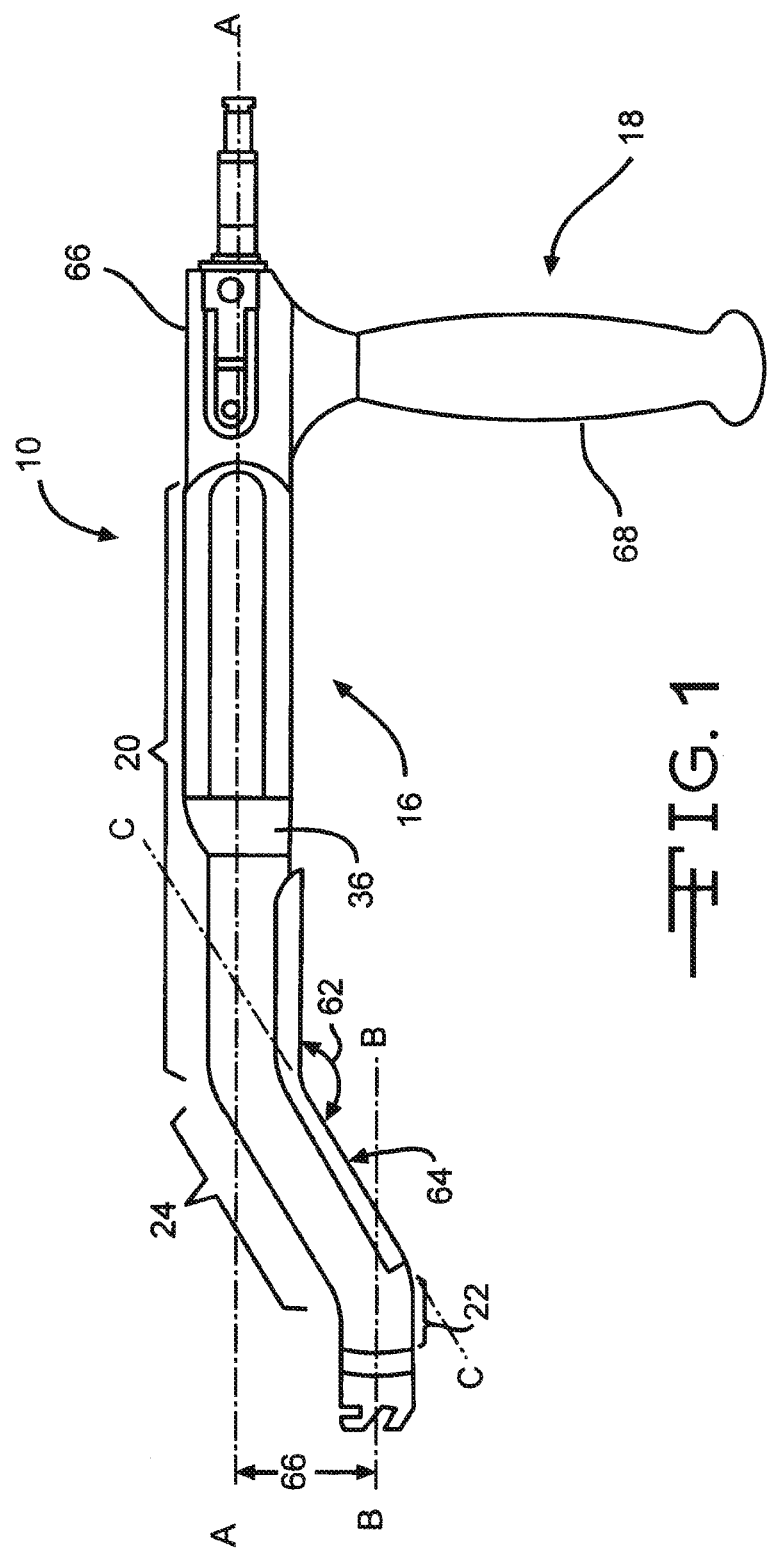
FIG. 1 illustrates an embodiment of the reamer spindle of the present invention.
Figure 2:
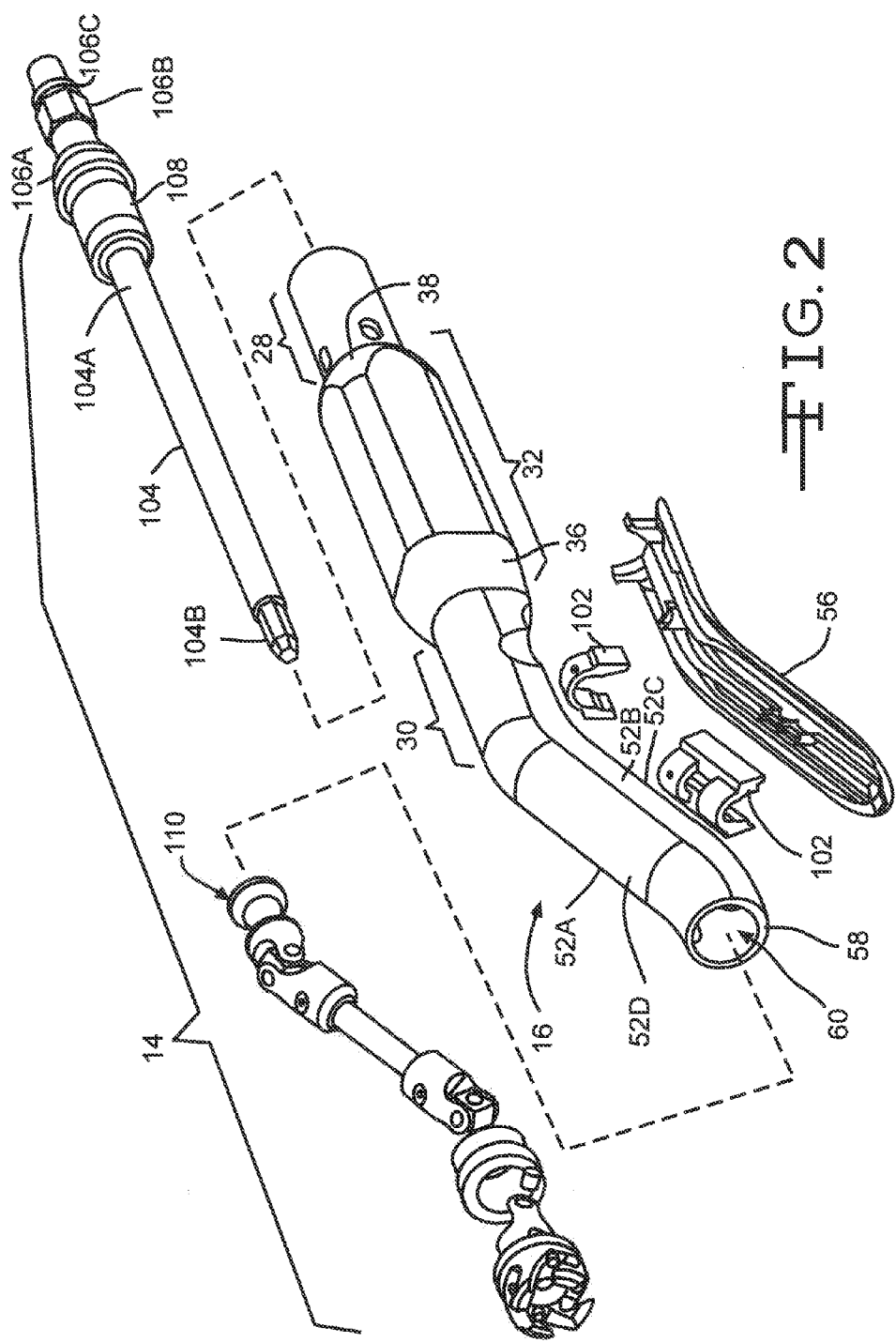
FIG. 2 shows an exploded view of the components comprising the reamer spindle.
Figure 12:
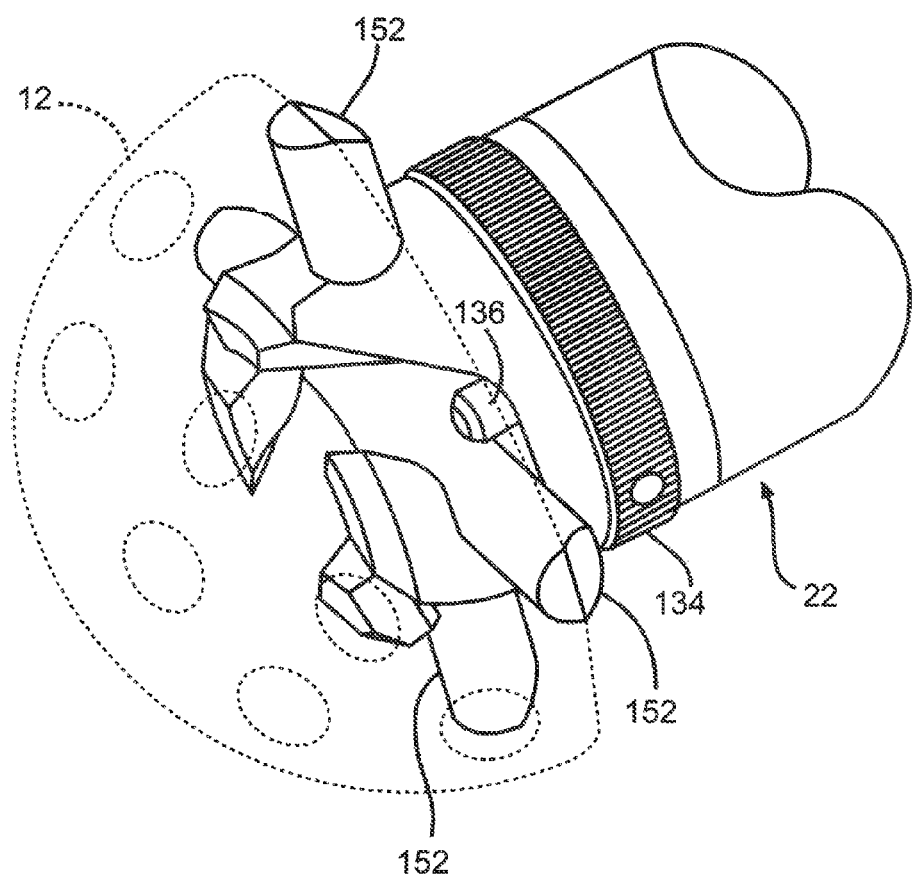
FIG. 12 is an enlarged perspective view of the distal U-joint 128 and connection crown 140 in a closely spaced relationship with a reamer 12 shown in phantom attached thereto.

Turning now to the drawings, FIGS. 1 and 2 illustrate a reamer spindle 10 according to the present invention. The reamer spindle 10 is connectable to a reamer 12 (FIG. 12) for performing a minimally invasive hip replacement surgery. The reamer spindle 10 generally comprises a drive train 14 disposed within a housing 16. A handle assembly 18 is adjustably connected to the housing 16 spaced from the reamer 12.

The housing 16 has a length that extends from a proximal end portion to a distal end portion. Specifically, the housing 16 extends from a main housing section 20, located at the proximal end portion, to a distal neck section 22 with an intermediate housing section 24 therebetween. An opening 26 resides within the housing that extends from the main housing section 20 through the distal neck section 22.

The main housing section 20 further comprises a proximal main housing portion 28, a distal main housing portion 30 and a central main housing portion 32 therebetween (FIG. 2). As shown in FIG. 1, the main housing section 20 extends along longitudinal axis A-A.

Figure 7:
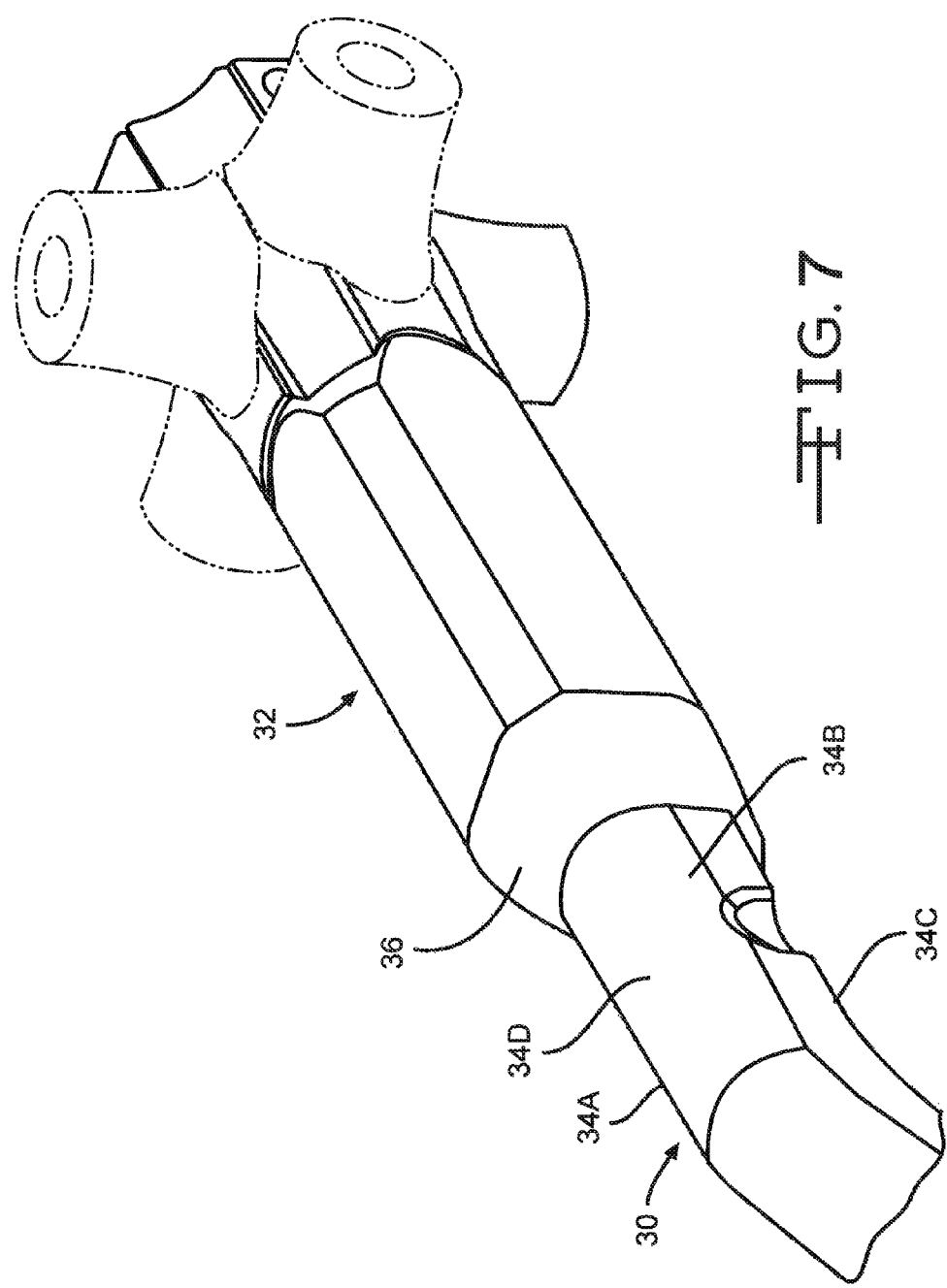
FIG. 7 illustrates embodiments of various orientations of the handle assembly with respect to the housing.

As shown in FIG. 7, the distal main housing portion 30 comprises spaced apart right and left side walls 34A and 34B extending upwardly from a bottom wall 34C to a top wall 34D. In a preferred embodiment, the right and left side walls 34A and 34B fluidly transition to a top wall 34D. This construction provides the distal main housing portion 30 with a generally rectangular-shaped cross-section. In a further preferred embodiment, the top wall 34D has a beveled top surface.

The central main housing portion 32 resides proximally of the distal main housing portion 30. The right and left side walls 34A, 34B and the bottom and top walls 34C, 34D of the distal main housing portion 30, extend proximally to form the walls of the central main housing portion 32. Similarly to the distal main housing portion 30, the central main housing portion 32 has a generally rectangular-shaped cross-section. In a preferred embodiment, the central housing portion 32 has a greater width and height as compared to the distal main housing portion 30.

In a further preferred embodiment, a first frustro-conical transition portion 36 resides between the distal main housing portion 30 and the central main housing portion 32. The first frustro-conical transition portion 36 forms a fluid transition between the distal main housing portion 30 and the central main housing portion 32. A second frustro-conical transition portion 38 (FIG. 4) resides between the central main housing portion 32 and the proximal main housing portion 28. The second frustro-conical transition portion 38 forms a fluid transition between the central portion 32 and the proximal main housing portion 28.

The proximal main portion of the 28 of the main housing section 20 resides proximally of the central main housing portion 32. The proximal main portion 28 further comprises an annular extension 40 (FIG. 4) that extends proximally from the second frustro-conical transition portion 28. The extension has an annular wall 42 with a curved cross-section. More preferably, the extension 40 comprises a circular cross-section. Although a circular cross-sectional geometry is preferred, the extension may comprise any of a non-limiting geometry including a rectangular, a hexagon, a triangular or the like. In a preferred embodiment, the annular extension wall 42 has an outer diameter 44 ranging from about 15 mm to about 20 mm, an inner diameter 46 ranging from about 10 mm to about 15 mm, and an extension throughbore 48 therebetween. The extension fluidly extends proximally from a larger diameter second frustro-conical transition portion 38 to the smaller diameter of the annular extension wall 42. The throughbore 48 preferably extends co-axially with the longitudinal axis A-A.

Figure 4:
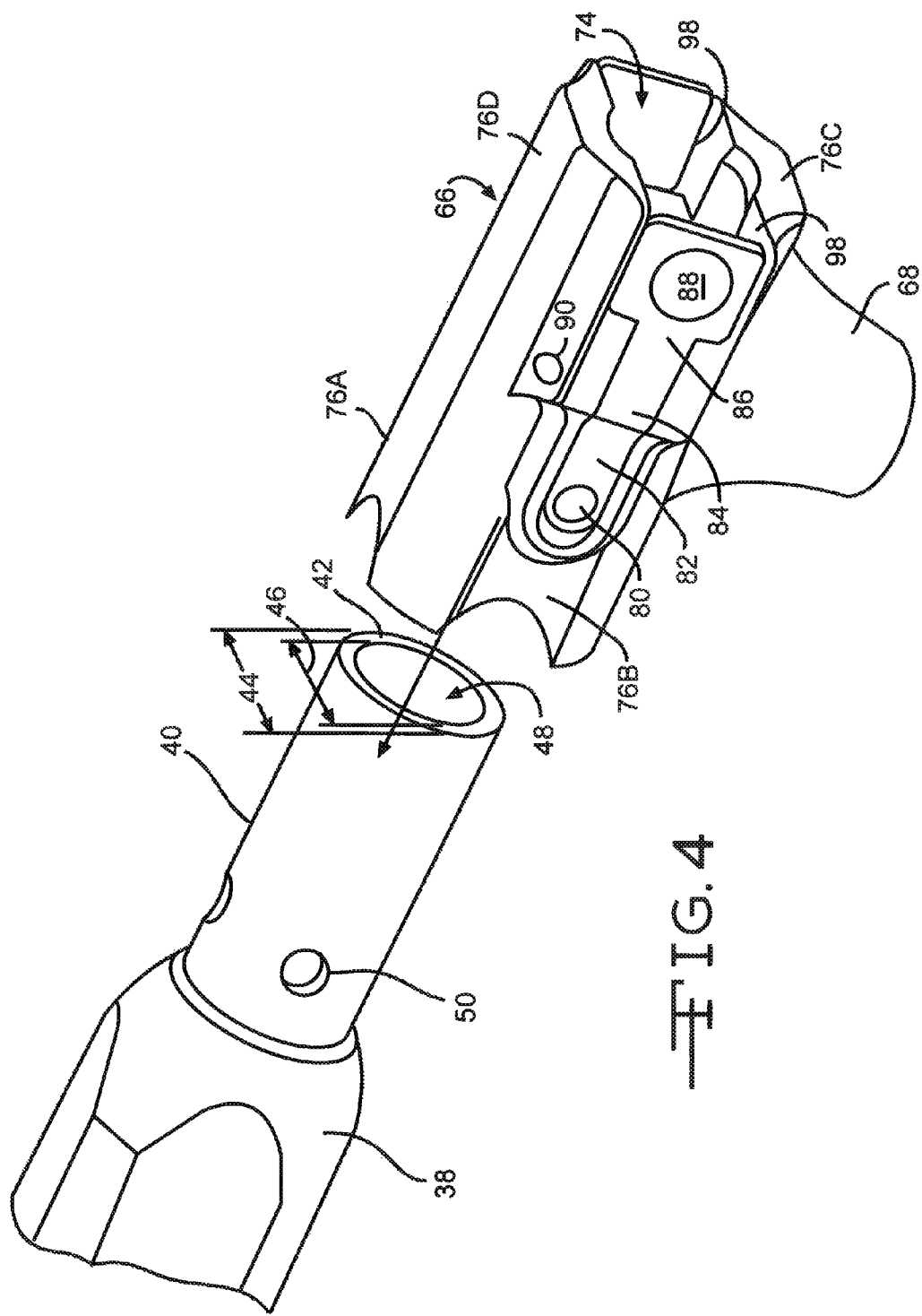
FIG. 4 illustrates a magnified view illustrating an embodiment of attaching the handle assembly to the housing.

A series of extension openings 50 are preferably positioned through the annual wall of the housing extension 42. In a preferred embodiment, four openings 50 are positioned through the annular wall 42 of the extension 40. The openings 50 are positioned circumferentially around the extension 40 such that they are oriented about perpendicular from each other. It should be noted that the reamer spindle 10 may be designed with more or less than four openings and that they may be positioned anywhere along the surface as shown in FIG. 4. As will be discussed in more detail, these openings 50 form a means of attachment of the handle assembly 18 to the housing 16.

Figure 8:
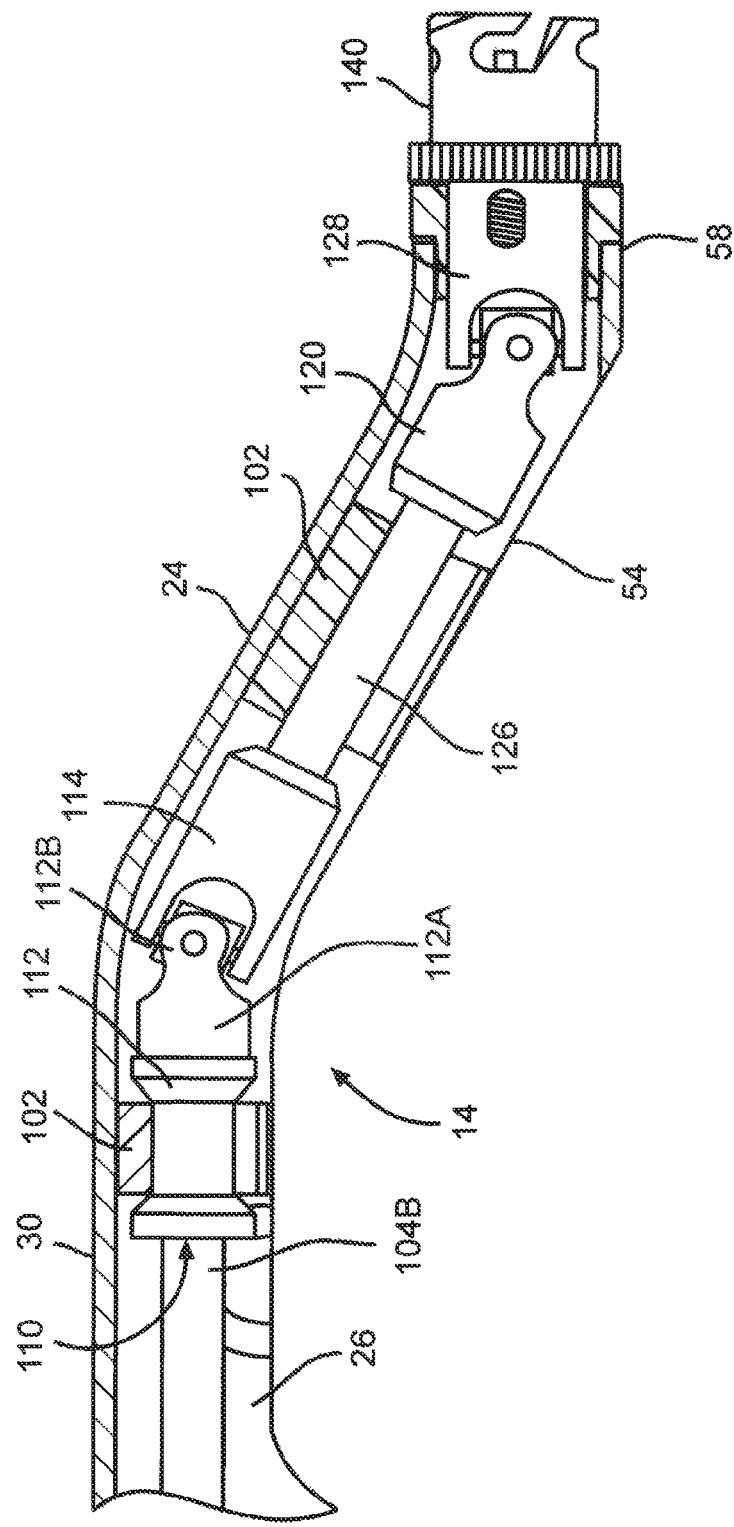
FIG. 8 is a cross-sectional view of a portion of the drive train residing within the housing.

As shown in FIG. 1, the intermediate housing section 24 extends distally from the main housing section 20 and proximally from the distal neck section 22. The intermediate housing section 24 comprises spaced apart right and left side walls 52A and 52B extending upwardly from a bottom wall 52C to a top wall 52D. This construction provides the intermediate section 24 with generally rectangular-shaped cross-section. In a preferred embodiment, an intermediate housing opening 54 may be positioned through the bottom wall 52C of the intermediate section 24 (FIG. 8). More preferably, this opening 54 may extend through the bottom wall of the intermediate housing section 24 and a portion of the distal main housing portion 30. A removable access cover 56 (FIG. 2) may be positioned over the opening 54. This access cover 56 prohibits debris from entering the housing 16 and provides easy access for cleaning the drive train 14 therewithin.

As shown in FIGS. 1 and 2, the distal end of the intermediary section 24 fluidly extends distally into the distal neck section 22. In a preferred embodiment, the distal neck section comprises a distal annular wall 58 with an outer diameter ranging from about 15 mm to about 20 mm, an inner diameter ranging from about 10 mm to about 15 mm, and a distal neck opening 60 therethrough. At the opposite end, the proximal end of the intermediate housing section 24 fluidly transitions into the distal end 30 of the main housing section 32. The left and right side walls 52A, 52B and the bottom and top walls 52C, 52D of the intermediary section 24 fluidly transition proximally into the distal main housing portion 30.

The intermediate housing section 24 is angled from the main housing section 32. An intermediate housing angle 62 is formed between the intersection of an imaginary line C-C that extends tangentially along a bottom surface 64 of the intermediate housing section 24 and longitudinal axis A-A (FIG. 1). In a preferred embodiment, the intermediate housing angle 62 ranges from about 20° to about 40°, more preferably, the intermediate housing angle 62 is about 30°. The intermediate housing section 24 forms an offset between the main housing section 32 and the distal neck section 22 which extends parallel along longitudinal axis B-B. In a further embodiment, an offset distance 66 between longitudinal axes A-A and B-B ranges from about 2 cm to about 5 cm.

It should be noted that it is preferred that the different sections comprising the housing 16 of the reamer spindle 10 are constructed such that they fluidly transition into each other. The distal neck section 22 transitions into the intermediate section 24 which transitions into the main housing section 32. The side walls 52A, 52B, top wall 52C, and bottom wall 52D of the intermediate housing section 24 extend distally to the distal neck section 22 of the spindle 10.

As shown in FIGS. 1 and 3 to 6, the handle assembly 18 of the present invention comprises a handle head portion 66 and a handle gripping portion 68. The handle head portion 66 is positioned about perpendicular to the handle gripping portion 68. The handle head portion 66 is constructed such that it is removably connectable to the curved housing extension portion 40 residing at the proximal end of the main housing section 32. The handle assembly 18 is composed of a durable lightweight material such as a polymeric material. More preferably, the handle assembly 18 may be composed of carbon fiber.

The handle head portion 66 comprises a distal handle head portion 70 spaced apart from a proximal handle head portion 72, a handle throughbore 74 extends therebetween. The handle head portion 66 further comprises a right handle wall 76A spaced apart from a left handle wall 76B. A bottom handle wall 76C is spaced apart from a top handle wall 76D. This construction provides the handle head portion 72 with a generally rectangular cross-section.

In a preferred embodiment, the handle throughbore 74 has a curved cross-section and more preferably has a round cross-section. The throughbore 74 is preferably dimensioned such that the housing extension 40 is positionable therewithin. In a preferred embodiment, the housing extension 40 is advanced through the handle throughbore 74.

The proximal end of the handle head portion 72 comprises an annular recess 78 that is designed to be fitted to the second frustro-conical transition portion 38 of the main housing section 32. When the handle assembly 18 is positioned over the housing extension 40, the handle head portion 66 is positioned about parallel to longitudinal axis A-A. Furthermore, the left and right walls as well as the top and bottom walls of the main housing section 32 and the handle head portion 66 are fitted about parallel to each other.

A pin 80, residing within the handle head portion 66, is designed to be positioned within one of the openings 50 of the housing extension 40. The pin 80, which is preferably positioned about perpendicular to longitudinal axis A-A, is attached to a distal end portion 82 of a handle lever 84. The handle lever 84 further comprises a lever proximal end portion 86 that is spaced from the distal end portion 82 of the handle lever 84. The proximal end portion 86 of the handle lever 84 comprises a thumb recess 88 within its outer surface. In a preferred embodiment, two pins 80, each residing at the distal ends of their respective handle levers 84, are positioned opposing each other. This preferred pin orientation enables the handle assembly 18 to be in a more secure engagement with the housing 16.

Figure 3:
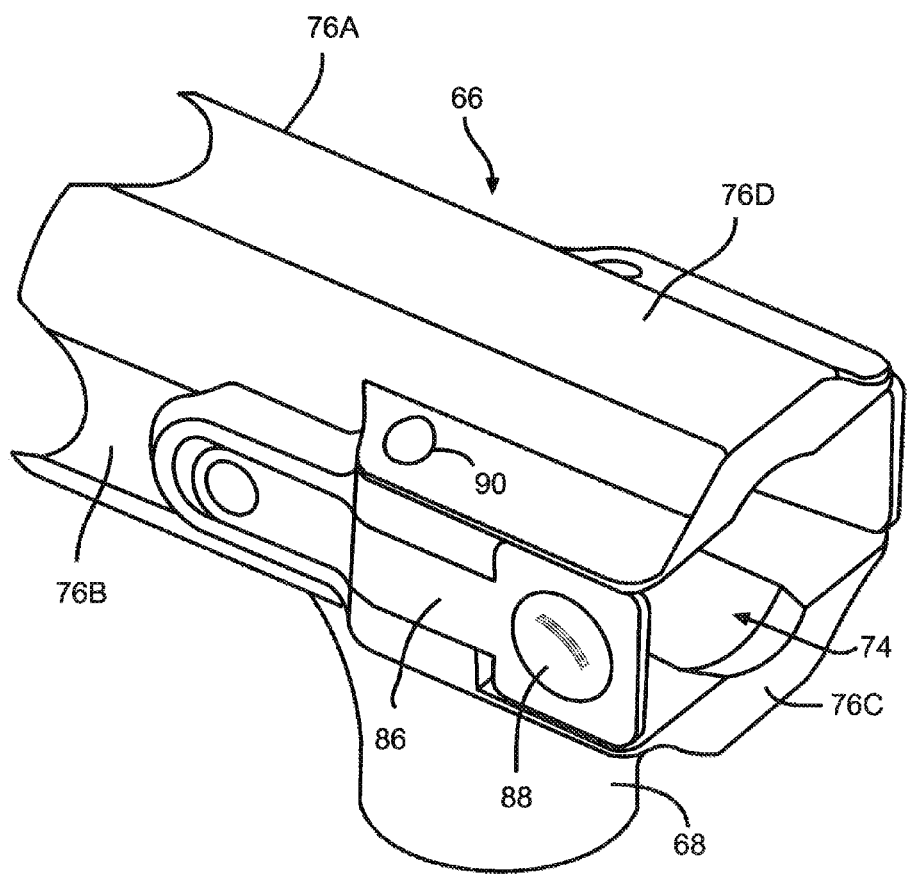
FIG. 3 shows a magnified view of an embodiment of the housing assembly of the present invention.
Figure 5:
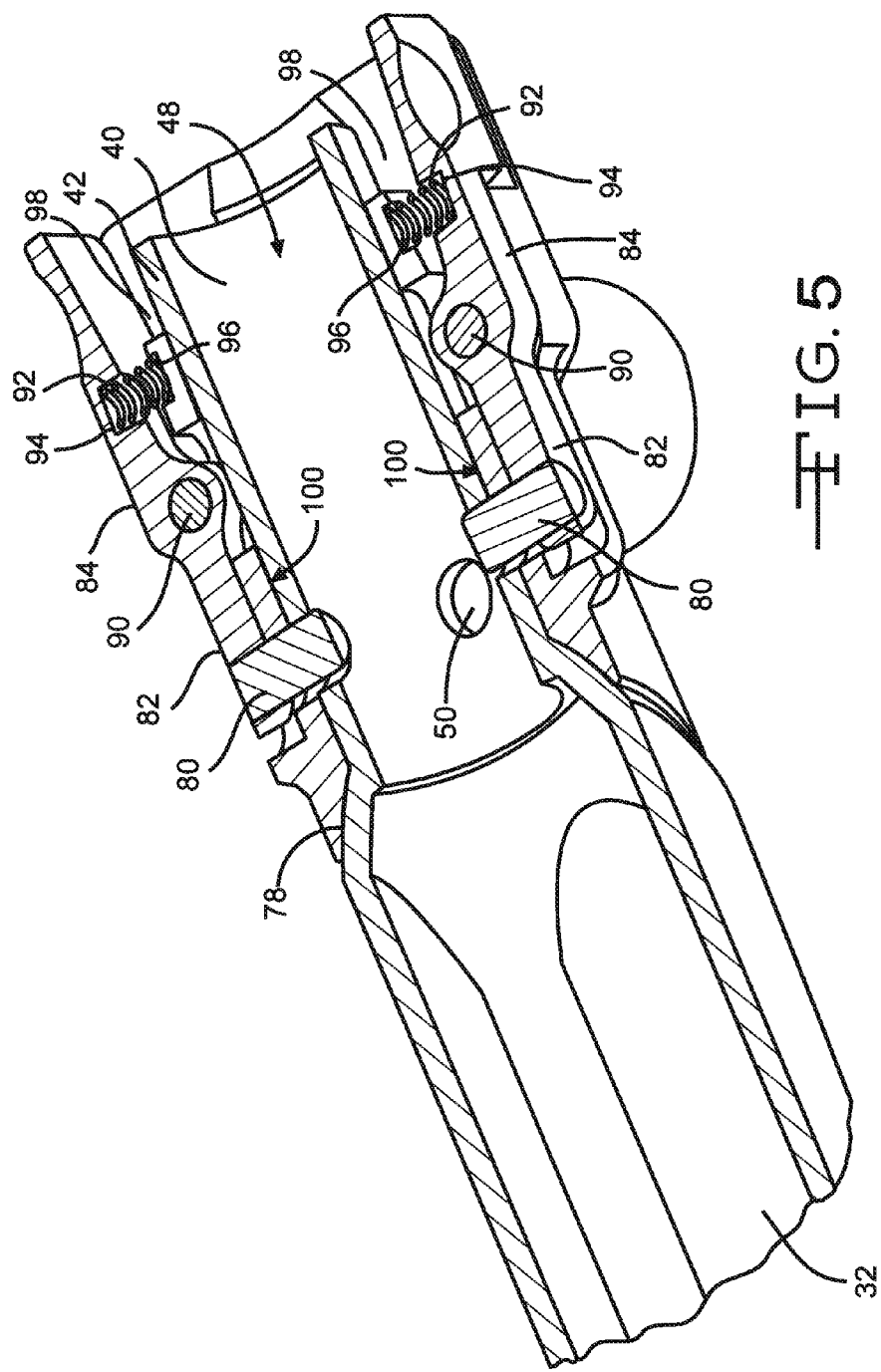
FIG. 5 is a cross-sectional view of an embodiment of the handle assembly connected to the housing.
Figure 6:
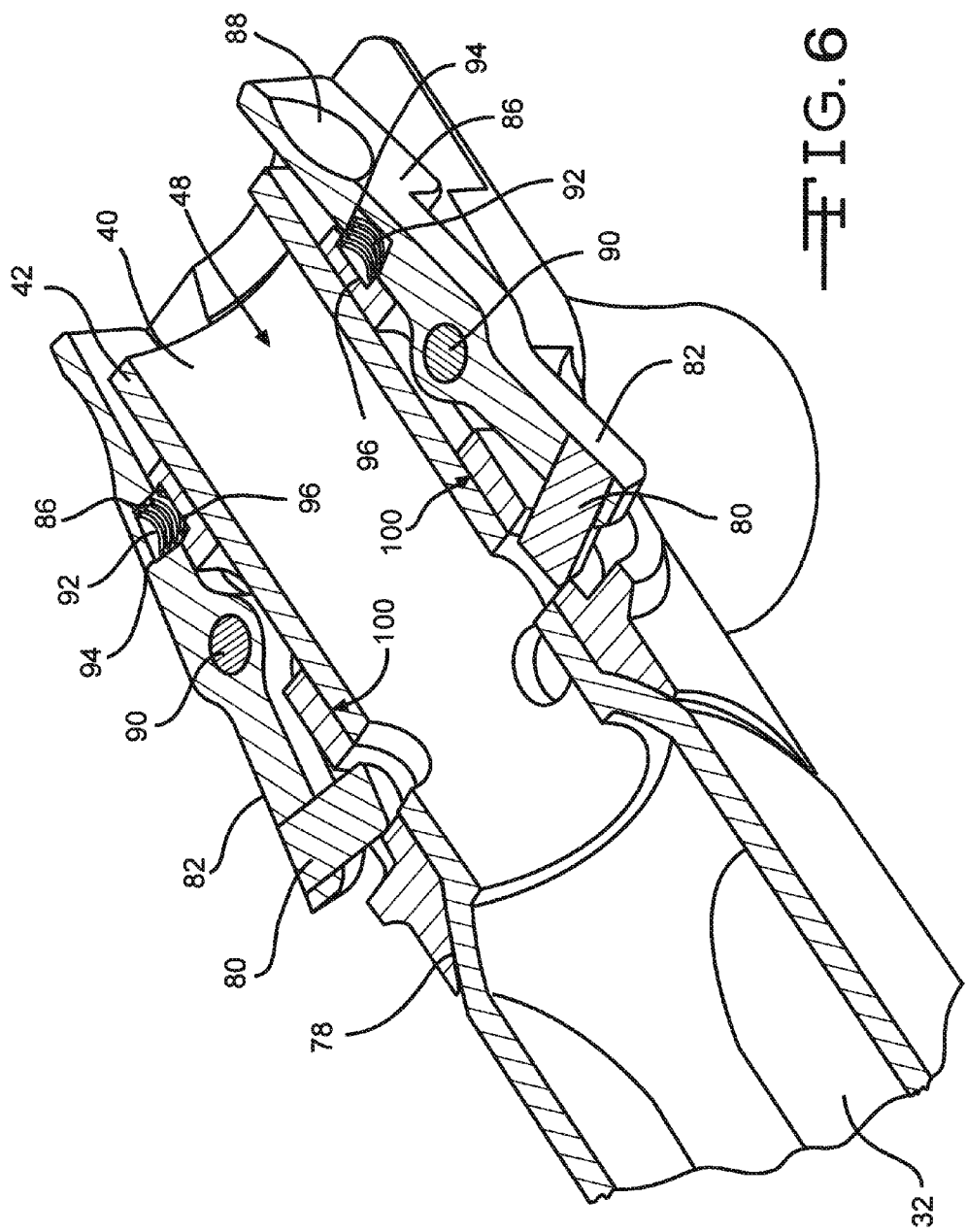
FIG. 6 shows a cross-sectional view of an alternate embodiment of the handle assembly connected to the housing.

As shown in FIGS. 3, 5, and 6, each handle lever 84 pivots about a handle pin 90 that resides between the distal 82 and proximal end portions 86 of the handle lever 84. The pin 90 is further positioned through the thickness of the lever 84, perpendicular to longitudinal axis A-A.

A spring 92 is preferably positioned between the body of the handle head portion 66 and the proximal end portion of the handle lever 84. The spring 92 is further positioned such that one end of the spring 92 resides within a recess 94 disposed within an inner surface of the proximal end portion 86 of the handle lever 84. The opposite end of the spring 92 resides in a recess 96 within an outer surface of the body of the handle head portion 66. The spring 92 acts as a bias between the inner surface of the proximal end portion of the handle lever 84 and the body of the handle head portion 66.

The handle assembly 18 is designed such that when a force is applied to the proximal end portion 86 of the handle lever 84, such as by pressing the lever with a thumb, the proximal lever end moves towards the outer surface of the handle head portion 66. Specifically, when the force is applied to the proximal end, the lever 84 pivots about the handle pin 90 such that the distal end 82 of the lever moves in an opposite direction of that of the lever's proximal end. The distal end 82 of the lever 84 moves away from the outer surface of the handle head portion 66 as shown in FIG. 6. Since the lever pin 80 is connected to the distal end portion 82 of the handle lever 84, the pin 80 is pulled out of the extension opening 50 and moves within the wall thickness of the handle head portion 66. At the same time, the proximal end 86 of the handle levers 84 moves through respective lever cutout portions 98 to enable unobstructed movement and full pivoting action of the handle levers.

Thus, the handle assembly 18 can be positioned such that the extension 40 of the main housing section 32 is positioned within the throughbore 74 of the handle head portion 66. Once the extension is positioned within the throughbore 74, the force applied to the proximal end portion of the handle lever 84 is released, thereby allowing the lever pin 80 to move proximally towards the housing extension 40. The spring 92 provides the biasing force against the proximal end portion of the handle lever 84 that returns the lever 84 to its initial position, about parallel to longitudinal axis A-A.

In a preferred embodiment, when the lever is returned to its initial position, the lever pin 80 extends past an inner wall surface 100 of the handle head portion 66. Furthermore, the pin 80 is positioned through one of the openings 50 of the housing extension 40, engaging the handle assembly 18 therewithin. Once the lever pin 80 is positioned within the opening 50 of the extension 40, the handle assembly 18 is in a locked relationship with the housing 16 of the spindle 10. The handle assembly 18 can be disengaged from the housing 16 of the spindle 10 by depressing the proximal end portion 86 of the handle lever 84 as shown in FIG. 6. The handle lever 84 therefore, enables the pin 80 to pivot out of the extension opening 50 and disengage the handle assembly 18 from the housing 16.

The handle assembly 18 can be positioned in a multitude of non-limiting orientations with respect to the main housing section 32. In a preferred embodiment, the handle assembly 18 can be positioned at 90° intervals about the circumference of the housing extension 40 as shown in FIG. 7. In a preferred embodiment, the opposing pins 80 of the handle assembly 18 are positioned within opposing openings 50 that extends through the annular wall 42 of the housing extension 40.

As previously mentioned, the drive train 14 resides within the housing 16 of the reamer spindle 10 of the present invention. A series of brackets 102 (FIGS. 2 and 8) may be used to hold the drive train 14 in place within the housing 16. In a preferred embodiment, the drive train 14 extends from the distal neck portion 22 through the proximal end portion of the housing extension 40.

Figure 9:
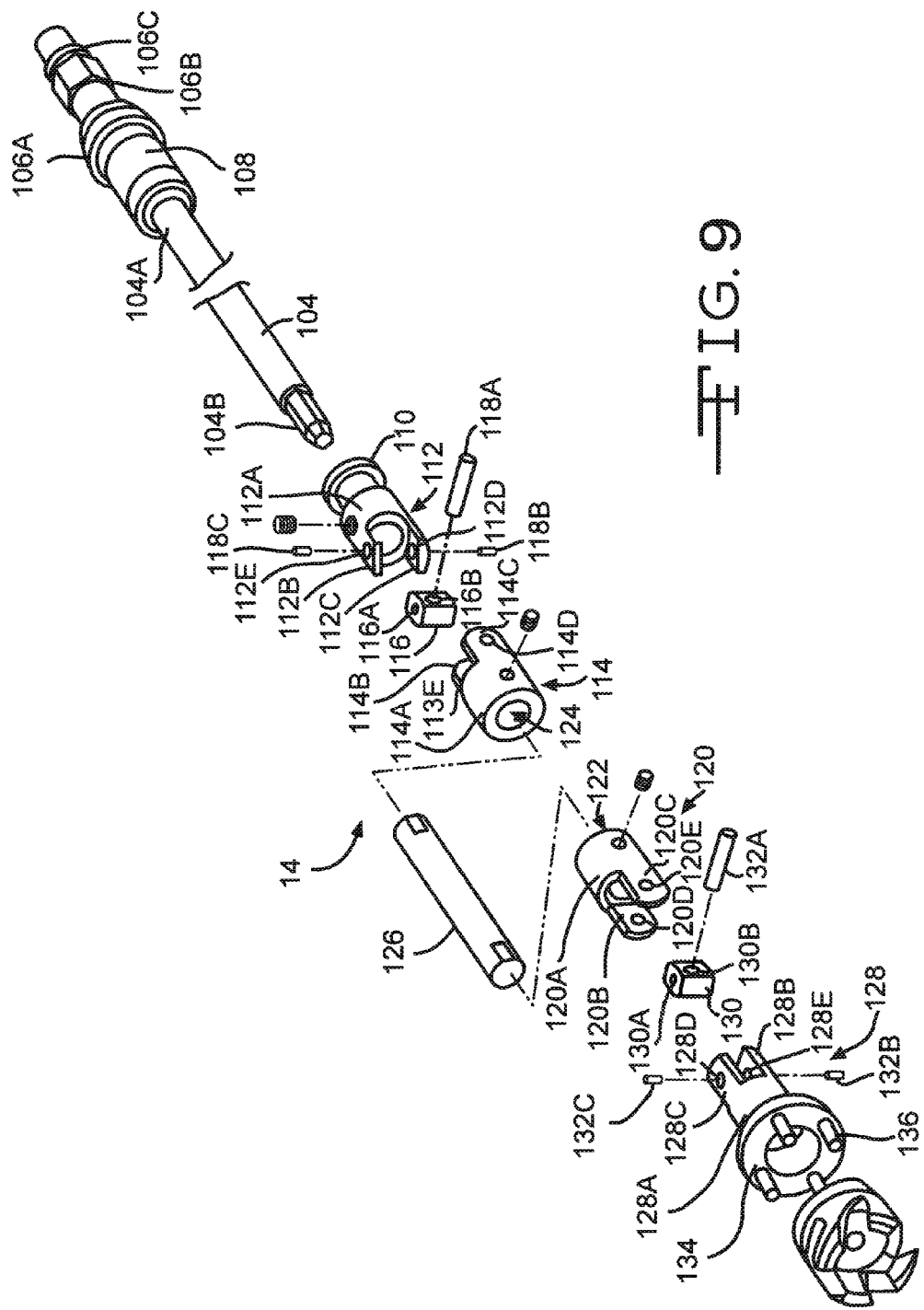
FIG. 9 is an exploded view of the components that comprise the drive train of the present invention.
Figure 10:
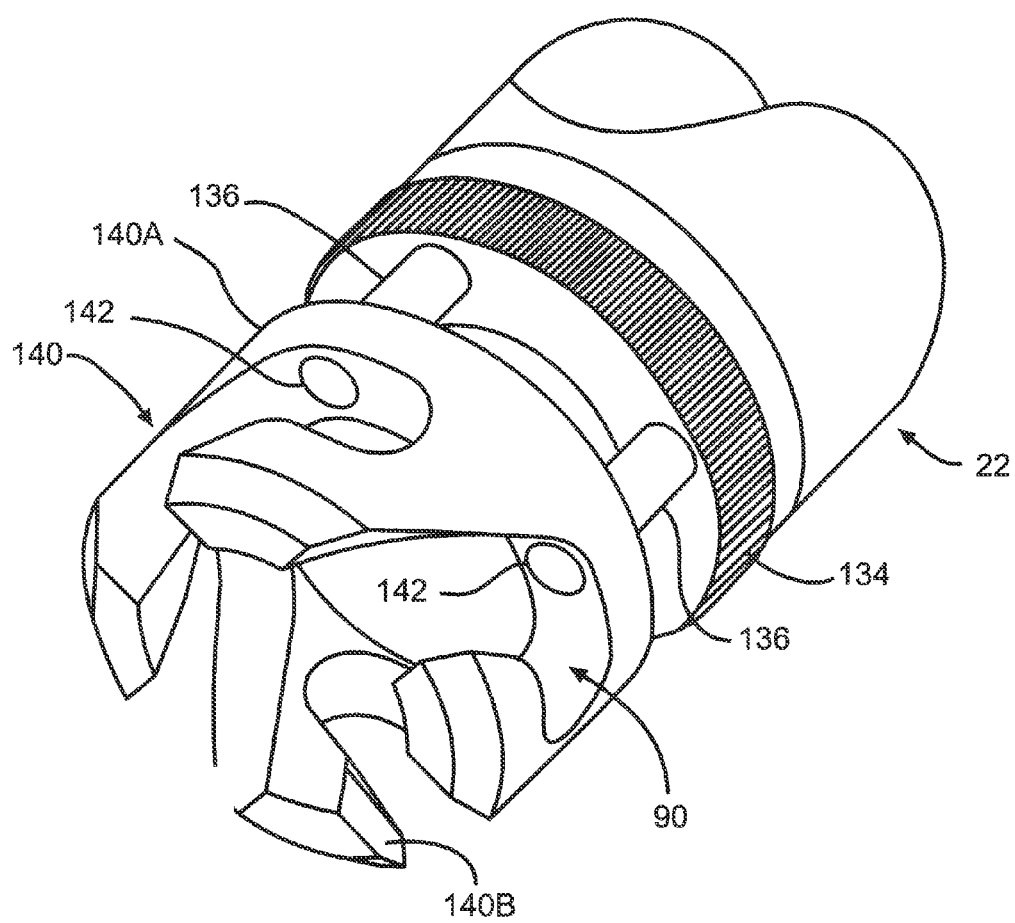
FIG. 10 is a magnified view of an embodiment of the distal end of the reamer spindle of the present invention.

As particularly shown in FIGS. 8 and 9, the drive train 14 comprises a series of interconnected U-joints, pivot blocks and pins in a pivotable relationship. A drive shaft 104 as a cylindrically-shaped member having a proximal portion 104A and a distal end portion 104B with a length there between is in a releasable connection with the drive train 14. The proximal shaft portion 104A comprises a series of cylindrical sections 106A, 106B and 106C that step down in diameter as they progress toward the proximal end 104A of the shaft 104. In a preferred embodiment, cylindrical section 106B has a hexagonal or similar type structure that provides flats for detachable connection to the chuck of a source of rotary drive power (not shown).

As illustrated in FIGS. 1, 2, and 9, the drive shaft 104 is positioned about parallel or co-axially to longitudinal, axis A-A, with a portion of its proximal end extending proximally past the handle assembly 18. The proximal portion 104A of the drive shaft 104 also comprises a sleeve 108 (FIG. 8) that is positioned distal of the series of cylindrical sections 106A, 106B, and 106C. In a preferred embodiment, the sleeve is positioned about the circumference of the shaft 104 such that it is in contact with the end of the annular wall 42 of the housing extension 40. The sleeve 108 is further constructed such that it is in a rotatable relationship about the shaft 104. The sleeve is preferably constructed of a polymeric material that provides mechanical wear resistance. Although a polymeric material is preferred, other materials such as metal or ceramic may also be used to construct the sleeve 108.

The distal end 104B of the drive shaft 104 comprises a hexagonal or similar structure that provides flats for detachable connection to the drive train 14. In a preferred embodiment, the distal end 104B of the drive shaft 104 is in a detachable connection with a socket end 110 of the drive train residing with the housing 16.

As particularly shown in FIGS. 8 and 9, a first or proximal U-joint 112 is supported at the distal end 104B of the shaft 104. In a preferred embodiment, the distal end 104B of the shaft 104 engages within the socket end 110 of the first or proximal U-joint 112. The proximal U-joint 112 is further comprised of a proximal cylindrical side wall 112A supporting a pair of yoke plates 112B and 112C having respective openings 112D, 112E.

A second U-joint 114 is positioned distal of the first U-joint 112. The second U-joint comprises a second side wall 114A supporting a pair of yoke plates 114B, 114C. The second U-joint 114 is positioned such that its pair of yoke plates 114B, 114C oppose the yokes plates 112B, 112C of the first U-joint 112. A proximal pivot block 116 (FIG. 9) resides between the yoke plates 112B, 112C of the proximal U-joint 112 and the pair of yoke plates 114B, 114C of the second U-joint 114. The proximal pivot block 116 comprises two pairs of perpendicularly opposed openings 116A and 116B.

Pins 118A are received in the openings 112D, 112E in the yoke plates 112B and 112C of the proximal U-joint 112 and the opening 116A in the pivot block 116, and a pin 116B is received in the opening 116B of the pivot block 116 and the openings 114D, 114E of the yoke plates 114B, 114C of the second U-joint 114 to thereby pivotably secure the proximal U-joint 112 to the second U-joint 114. It is noted that only one of the pins 118A or 118B extends completely from one face of the pivot block 116 to the other face. As passage from one face to the other is blocked by the first pin, the other of the two pins 118A or 118B is two "half pins".

As shown in FIG. 9 the drive train 14 also includes a third U-joint 120 that comprises a third cylindrical side wall 120A supporting a pair of yoke plates 120B and 120C having respective openings 120D, 120E. The third U-joint 120 is positioned such that a third U-joint receiving end 122 opposes a receiving end 124 of the second U-joint 114. An intermediary rod 126 is positioned between the second and third U-joints 114, 120, preferably within the respective receiving ends 122, 124.

The drive train 14 comprises a distal or fourth U-joint 128 that is positioned distal of the third U-joint 120. The distal U-joint 128 comprises a distal sidewall 128A supporting a pair of yoke plates 128B, 128C and is further positioned such that its pair of yoke plates 128B, 128C oppose the yokes plates 120B, 120C of the third U-joint 120. A distal pivot block 130 (FIG. 9) resides between the yoke plates 120B, 120C of the third U-joint 120 and the pair of yoke plates 128B, 128C of the fourth U-joint 128. The proximal pivot block 130 comprises two pairs of perpendicularly opposed openings 130A and 130B.

Pins 132B, 132C are received in the openings 128D, 128E in the yoke plates 128B and 128C of the distal U-joint 128 and the opening 130A in the distal pivot block 130, and a pin 132A is received in the opening 130B of the distal pivot block 130 and the openings 120D, 120E of the yoke plates 120B, 120C of the third U-joint 120 to thereby pivotably secure the third U-joint 120 to the distal U-joint 128. Opposite the yoke plates, the cylindrical side wall 128A meets a base plate 134 having an enlarged diameter. A plurality of pins 136 extending outwardly from the base plate 134 have their respective axes aligned parallel to each other.

In this manner, the drive train 14 comprising the drive shaft 104, the first U-joint 112, the first pivot block 116, the second U-joint 114, the intermediary rod 126, the third U-joint 120, the distal pivot block 130 and the proximal U-joint 128 provides for transmission of rotational motion imparted to the proximal end of the shaft 104 to the base plate 134 and its supported pins 136.

Figure 11:
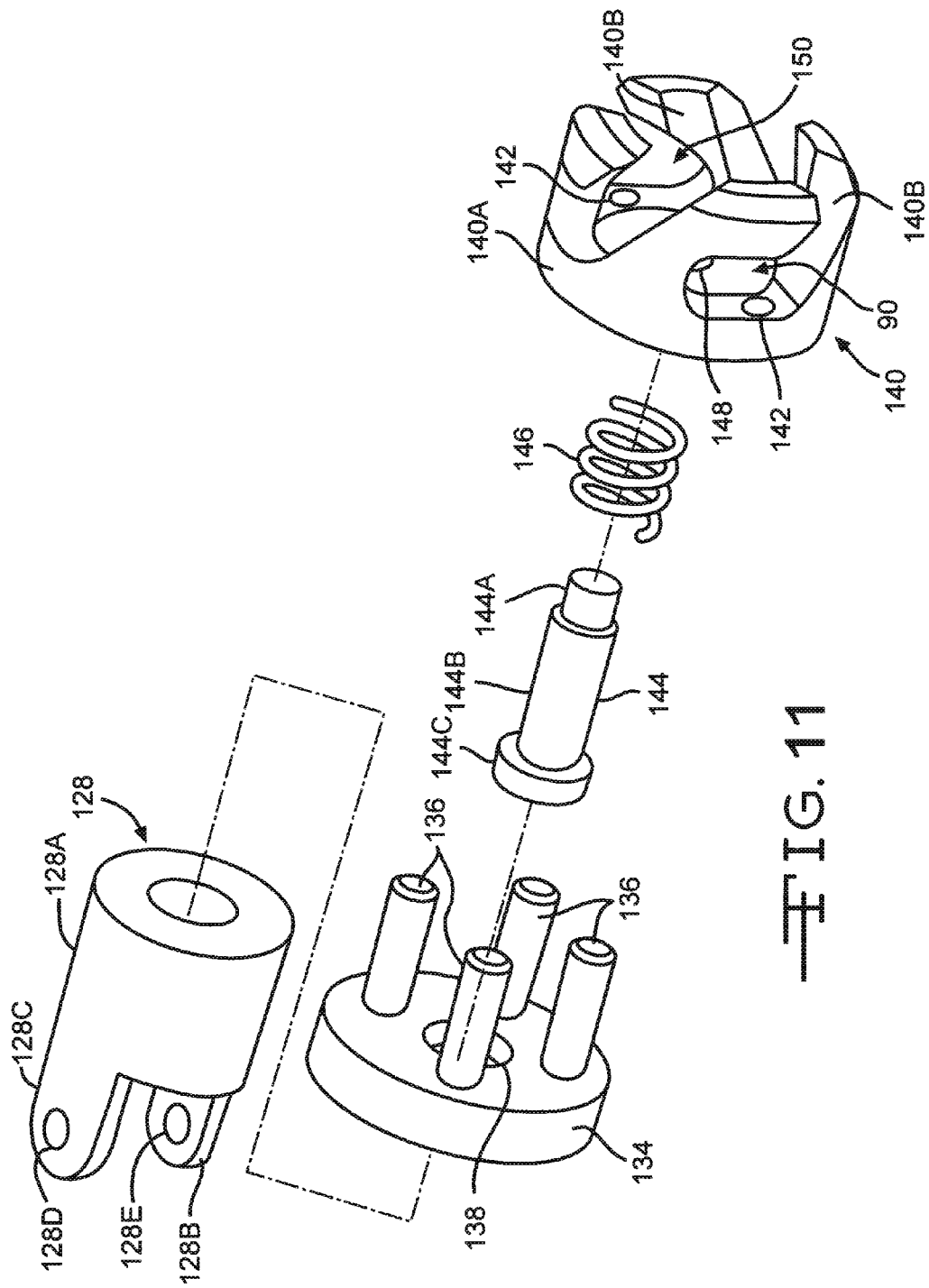
FIG. 11 is an exploded and enlarged view showing the connection structure of the distal U-joint 128 to a reamer connection crown 140.

As particularly shown in FIG. 11, the base plate 134 of the proximal U-joint 128 includes a central opening 138 completely through the thickness of the plate. A reamer connection crown 140 comprises a base plate 140A supporting a plurality of angled fingers 140B. Preferably, there are four angled fingers 140B. The plate 140A is provided with openings 142 that receive the pins 136 extending from the base plate 134 of the proximal U-joint 128.

An abutment pin 144 is a cylindrically shaped member having a first section 144A of a lesser diameter, an intermediate section 144B of an intermediate diameter and a larger diameter third section 144C. A coil spring 146 is received on the abutment pin 144 surrounding the intermediate section 144B. The spring 146 abuts against the third section 144C. The first section 144A of the pin 144 is received in a central opening 148 in the base 140A of the reamer connection crown 140 in a fixed manner.

One end of the coil spring 146 biases against the base plate 134 of distal U-joint 128. That is on the side of the plate 134 opposite the pins 136. The other end of spring 146 biases against the larger diameter section 144C of pin 144. However, since the first section 144A of the pin 144 is fixed to the base 140A of the crown 140, the crown is thereby tensioned into a secured relationship with the distal U-joint 128. The bias of spring 146 enables the distance between the connection crown 140 against the distal U-joint 128 to be manipulated between a closely-spaced relationship and a spaced apart position.

In that manner, the reamer 12 is removably fixed to the drive train 14 by manipulating the reamer connection crown 140 in an axial direction away from the distal U-joint 128 and against the biasing force of the spring 146. This creates separation between the crown 140 and the U-joint 128, which prior to manipulation are in the closely-spaced relationship, and removes the pins 136 from blocking access to the spaces 150 provided between the fingers 140B and the crown plate 140A. The connection structure, such as the cross-bars 152 (FIG. 12) of the reamer 12, is then capable of being received in these spaces 150. When the surgeon releases his grip on the crown 140, the spring 146 returns the connection crown to its original closely-spaced relationship against the plate 134 of the distal U-joint 128. The pins 136 are once again partially residing in the spaces 142 between the fingers 140B and the base plate 140A to thereby prevent unintended release of the reamer 12 from the drive train 14 of the reamer spindle 10. This connection structure is commonly referred to as a "bayonet-type" connection.

Figure 13:
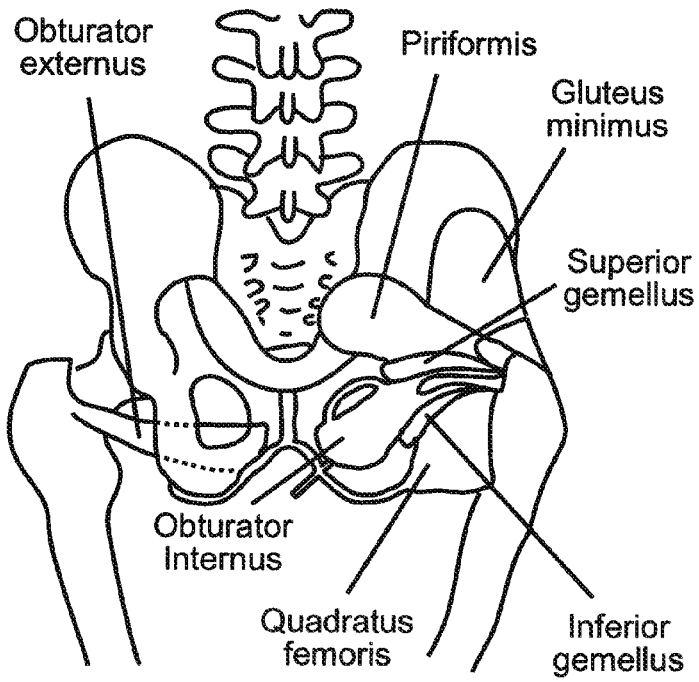
FIGS. 13 to 15 are schematic views of the anatomy of a human hip joint.
Figure 14:
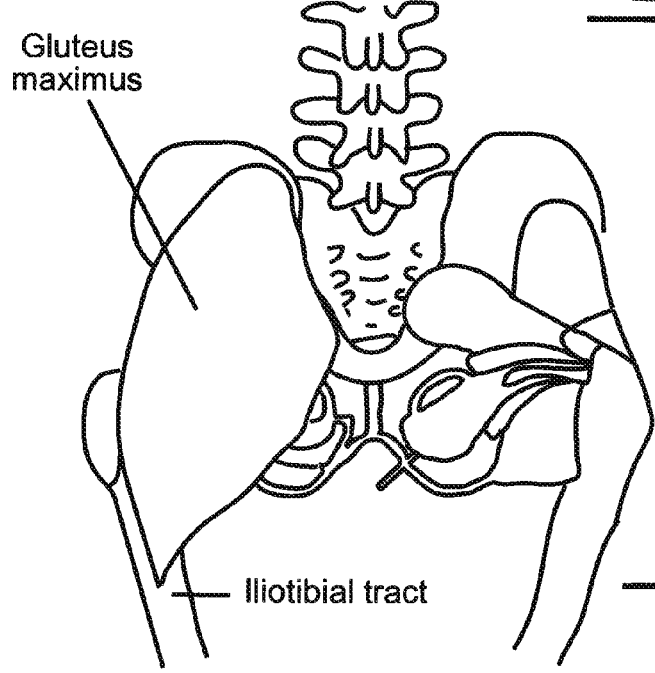
Figure 15:
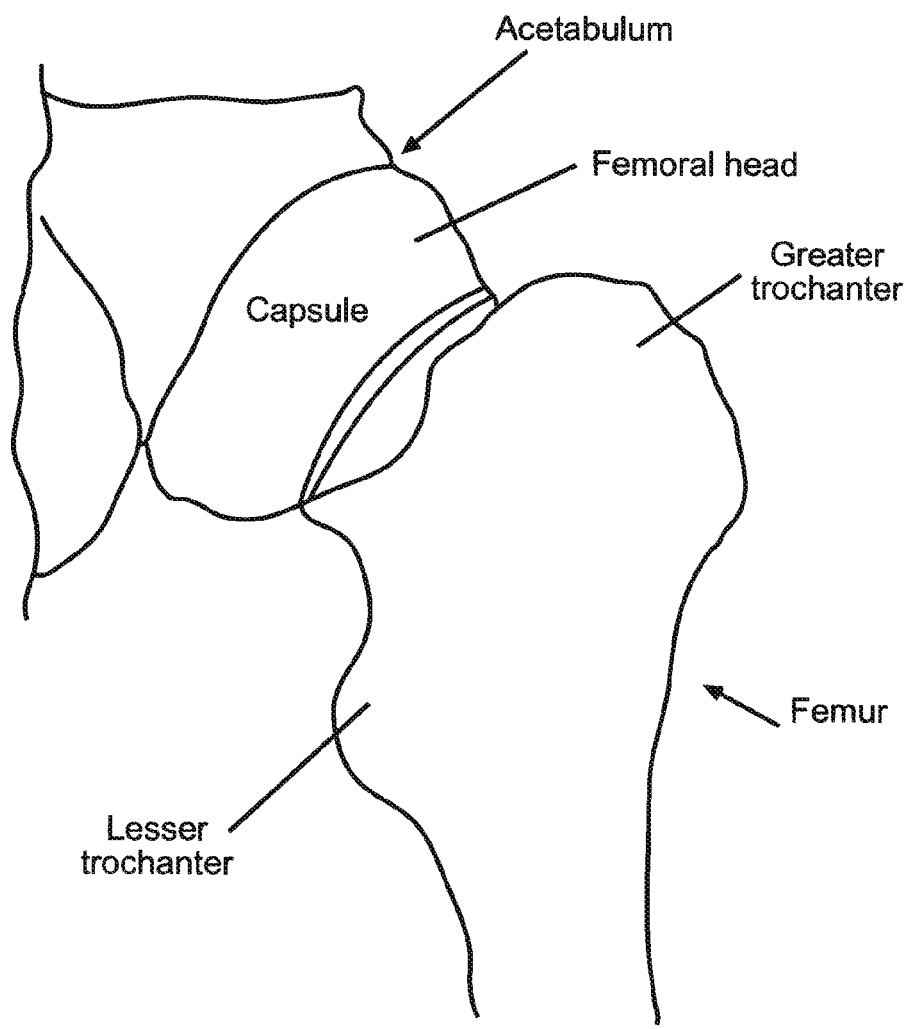

FIGS. 13 to 15 depict some features of the musculoskeletal anatomy of a human hip region. As shown in FIG. 13, there are several muscles that act to stabilize the femoral head of a femur bone in the acetabulum. Those include the short external rotator muscles (i.e., the piriformis, the superior gemellus, the obturator internus, the inferior gemellus obturator externus and the quadratus femoris). The gluteus maximus (see FIG. 14) extends over the short external rotator muscles. The femoral head is enclosed in a fibrous capsule (see FIG. 15), which attaches to the bone outside the acetabular lip and to the base of the neck of the femoral head.

The MIS posterior hip replacement approach has traditionally involved first a skin incision, followed by an incision in the fascia lata, and then detachment of the short external, rotator muscles of the hip (see FIG. 13). However, in a modified MIS posterior hip replacement approach, described further below, only the piriformis muscle or conjoined tendon needs to be detached.

Figure 16:
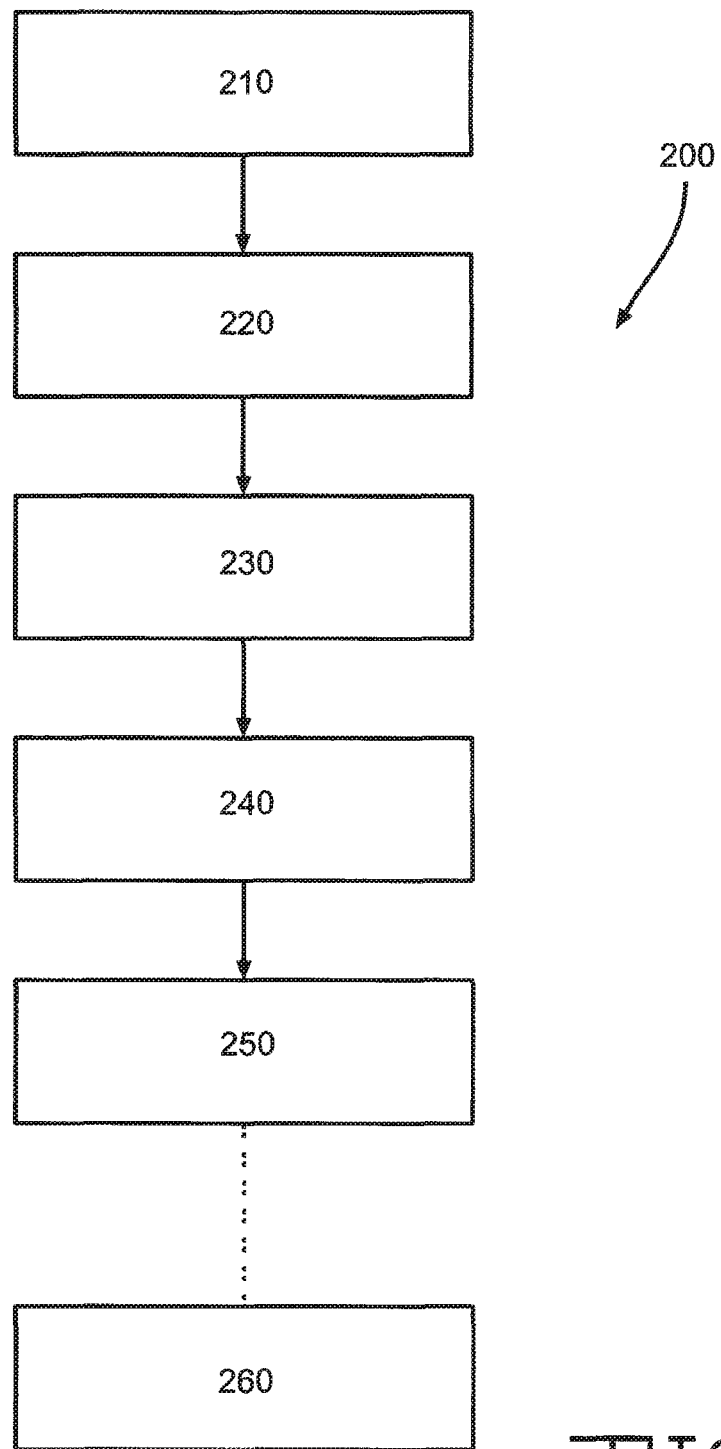
FIG. 16 is a block diagram illustrating steps in a minimally invasive hip replacement surgery using a posterior approach.

FIG. 16 is a schematic block diagram illustrating steps in a method 200 for using the reamer spindle 10 in a MIS hip replacement surgery. The surgeon begins by making an incision 210 in a posterior side of a patient's hip (e.g., on the buttocks) on a side proximate the hip joint to be treated. The surgeon then separates 220 fibers in the gluteus maximus longitudinally (i.e., not cut transversely) using a trans maximus approach to access the capsule. The present approach does not involve an incision in the fascia lata, which is required in other posterior surgical approaches. The surgeon then detaches 230 the piriformis or conjoined tendon, which is the only short external rotator muscle that is detached. This approach preserves the superior gemellus if it is not conjoined to the pirif tendon, obturator internus, inferior gemellus obturator externus and quadratus femoris, which provide significant additional stability to the hip. It is believed that such preservation also facilitates significantly faster post operative recovery. The surgeon then performs a capsulotomy 240 (e.g., L-shape or J-shape) to access the acetabulum. Once access to the acetabulum is achieved, the surgeon advances 250 the distal section 22 of the reamer spindle 10 supporting the reamer 12 through the incision to the surgical site proximate the acetabulum (see FIG. 17). The reamer spindle 10 is now operated to cut bone from the acetabulum (e.g. diseased bone) and prepare the acetabulum for implantation of a prosthetic acetabular cup. The femoral head is also removed and a prosthetic hip stem implanted into the femur, the prosthetic hip stem having a femoral ball head configured to articulatingly couple to the acetabular cup prosthesis. Once the prosthesis is in place, the capsule can be closed 260, followed by closure in the incisions to the gluteus maximus and skin.

The reamer spindle 10 is preferably configured for reuse, and can be disassembled for sterilization between uses. Disassembly is done by first depressing the handle lever 84 which disengages the pin or pins 80 from the opening 50 of housing extension 40. Once the handle assembly 18 is removed, the drive shaft 104 can be removed from the drive train 14 within the housing 16. After the drive shaft 104 is removed, the access panel 56 may be removed which allows access to the components comprising the drive train 14. Once the access panel 56 is removed, the reamer spindle 10 can be sterilized for reuse.

Additionally, the housing 16 is preferably made of a durable material that can be washed and sterilized (e.g., with high heat) to comply with sterilization standards known in the art. In one embodiment, the housing 16 is made of metal, such as stainless or a super alloy material. In another embodiment, the housing 16 is made of a composite material such as carbon fiber. Though the illustrated embodiment shows the housing 16 as being one piece, in other embodiments it can be modular to facilitate disassembly of the reamer spindle 10.

Preferably, the reaming angle should correlate as closely as possible to the intended angle of acetabular cup implantation.

Additionally, as discussed above, the length of the distal neck section 22 is preferably between about 25 mm and about 35 mm. This range is particularly advantageous in MIS hip replacement surgical procedures (e.g., the method illustrated in FIG. 16) in that during the surgical procedure the distal neck section 22 is in direct contact with the short external rotator muscles, which must be preserved to optimize the clinical outcome. The length of approximately 25-35 mm advantageously allows the reamer 12 to be positioned within the acetabulum while minimizing contact between the reamer spindle 10 (e.g., the distal neck section 22) and the short external rotator muscles of the hip, which are in the inferior aspect of the wound. Additionally, the thickness (e.g., outer diameter) of the housing 16, which is preferably between about 9 mm and about 16 mm also advantageously minimizes soft tissue trauma during advancement of the reamer spindle 10 through the incision to position the reamer 12 within the acetabulum.

Through the reamer spindle 10 is discussed above in connection with an MIS hip replacement posterior approach, one of the ordinary skill in the art will recognize that the reamer spindle 10 can be used in other MIS hip replacement surgical approaches, such as the anterior, antero-lateral, and postero-lateral approaches. Additionally, the reamer spindle 10 may also be usable in applications other than posterior MIS hip replacement procedures such as interior, interior-lateral and postero-lateral approaches, as well as shoulder replacement procedures. Though use of the reamer spindle 10 is described herein with respect to human hip replacement surgery, one of ordinary skill in the art will recognize that it may also be useful in animal hip replacement surgeries.

Of course, the foregoing description is that of certain features, aspects and advantages of the present invention, to which various changes and modifications can be made without departing from the spirit and scope of the present invention. Moreover, the reamer need not feature all of the objects, advantages, features and aspects discussed above. For example, in some embodiments, the casing of the reamer in the neck portion can be removed and/or replaced with a shield member to inhibit trauma to muscle tissue during operation of the reamer. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention.

What is claimed is:

1. A surgical reamer spindle, which comprises:
   a) a housing, comprising:
      i) a main housing section extending along a first longitudinal axis;
      ii) an intermediate housing section connected to a distal end of the main housing section;
      iii) a distal housing section connected to a distal end of the intermediate housing section; and
      iv) at least two spaced apart openings in the main housing section, the openings residing in a plane aligned perpendicular to the first longitudinal axis;
   b) a drive train at least partially housed inside the housing;
   c) a reamer connector extending distally from the drive train for releasable connection to a reamer;
   d) a handle assembly comprising a handle head portion supporting a handle grip, wherein the handle head portion defines a throughbore that receives the main housing section in a radially rotatable relationship with respect to the first longitudinal axis;
e) a locking mechanism supported by the handle head portion, the locking mechanism comprising:
   i) a lever pivotably supported by a pivot pin secured to the handle head portion, wherein the lever extends along a second longitudinal axis from a proximal lever portion to a distal lever portion, and wherein the second longitudinal axis is spaced from the first longitudinal axis of the main housing section;
   ii) a lever pin at the distal lever portion, the lever pin extending inwardly toward the first longitudinal axis; and
   iii) a spring positioned between the handle head portion and the proximal lever portion,
f) wherein the proximal lever portion is pivotably manipulatable about the pivot pin and against a bias of the spring to register the lever pin in a first one of the at least two openings in the main housing section to thereby provide the handle grip supported by the handle head portion in a first radially locked position with respect to the first longitudinal axis of the main housing section, and
g) wherein the proximal lever portion is further manipulatable about the pivot pin and against the bias of the spring to remove the lever pin from the first opening to thereby permit relative rotational movement of the handle grip connected to the handle head portion about the main housing section until the lever pin is aligned with the second one of the openings and then the proximal lever portion is manipulatable to cause the spring to bias the lever pin into registry with the second opening to thereby provide, with respect to the first longitudinal axis of the main housing section, the handle grip in a second radially locked position different than the first radially locked position.

2. The surgical reamer spindle of claim 1 wherein the lever resides at least partially within a recess in a sidewall of the handle head portion.

3. The surgical reamer spindle of claim 1 wherein there are four openings in the main housing section, the four openings being spaced at 90° intervals from each other in the plane aligned perpendicular to the first longitudinal axis.

4. The surgical reamer spindle of claim 1 wherein the locking mechanism comprises two levers pivotably secured to the handle head section, the levers being diametrically opposed to each other.

5. The surgical reamer spindle of claim 1 wherein the intermediate housing section is angled between the main housing section and the distal neck section.

6. The surgical reamer spindle of claim 5 wherein the intermediate housing section extends along a third longitudinal axis that is at an intermediate housing angle ranging from 20° to 40° with respect to the first longitudinal axis.

7. The surgical reamer spindle of claim 1 wherein the main housing section is offset from the distal neck section by an offset distance that ranges from 2 cm to about 5 cm, the offset distance defined as the distance between the first longitudinal axis extending along the main housing section and a fourth longitudinal axis extending along the distal neck section.

8. The surgical reamer spindle of claim 1 wherein the main housing section comprises a distal main housing portion spaced apart from a proximal main housing portion, a central main housing portion being therebetween.

9. The surgical reamer spindle of claim 8 wherein a first frustro-conical transition portion resides between the distal main housing portion and the central main housing portion.

10. The surgical reamer spindle of claim 8 wherein a second frustro-conical transition portion resides between the central main housing portion and the proximal main housing portion.

11. The surgical reamer spindle of claim 1 wherein the drive train comprises a drive shaft having a proximal drive shaft end spaced from a distal drive shaft end, the proximal drive shaft end being adaptable for releasable connection to a source of rotary motion.

12. The surgical reamer spindle of claim 1 wherein the drive train comprises a drive shaft having a proximal drive shaft end spaced from a distal drive shaft end, the proximal drive shaft end being adaptable for releasable connection to a source of rotary motion, a first, proximal U-joint rigidly connected to the distal drive shaft end and pivotably connected to a second U-joint connected to a proximal end of an intermediary rod residing in the intermediate housing section, wherein the pivotably connected first and second U-joints reside at a transition of the main housing section to the intermediate housing section.

13. The surgical reamer spindle of claim 12 wherein the drive train further comprises an intermediary rod residing in the intermediate housing section and comprising a proximal rod end rigidly connected to the second U-joint opposite the first U-joint, a third U-joint rigidly connected to a distal end of the intermediary rod and pivotably connected to a fourth, distal U-joint connected to the reamer connector, wherein the pivotably connection third and fourth U-joints reside at a transition of the intermediate housing section to the distal housing section.

14. The surgical reamer spindle of claim 1 wherein the handle assembly is at least partially composed of a polymeric material.

15. The surgical reamer spindle of claim 1 wherein the handle assembly is at least partially composed of a carbon fiber material.

16. The surgical reamer spindle of claim 1 wherein the reamer connector extending distally from the drive train comprises a bayonet-type connector.

17. The surgical reamer spindle of claim 1 wherein a proximal portion of the main housing section provided with the at least two openings and supporting the handle assembly is cylindrical.

18. A surgical reamer spindle, which comprises:
a) a housing, comprising:
   i) a proximal housing section extending to a distal housing section, wherein at least the proximal housing section extends along a first longitudinal axis; and
   ii) at least two spaced apart openings in the proximal housing section, the openings residing in a plane aligned perpendicular to the first longitudinal axis;
b) a drive train at least partially housed inside the housing;
c) a reamer connector extending distally from the drive train for releasable connection to a reamer;
d) a handle assembly comprising a handle head portion supporting a handle grip, wherein the handle head portion defines a throughbore that receives the main housing section in a radially rotatable relationship with respect to the first longitudinal axis;
e) a locking mechanism supported by the handle head portion, the locking mechanism comprising:
   i) a lever pivotable supported by a pivot pin secured to the handle head section, wherein the lever extends along a second longitudinal axis from a proximal lever portion to a distal lever portion, and wherein the second longitudinal axis is spaced from the first longitudinal axis of the main housing section;

ii) a lever pin at the distal lever portion, the lever pin extending inwardly toward the first longitudinal axis; and iii) a spring positioned between the handle head portion and the proximal lever portion, f) wherein the proximal lever portion is pivotably manipulatable about the pivot pin and against a bias of the spring to register the lever pin in a first one of the at least two openings in the main housing section to thereby provide the handle grip supported by the handle head portion in a first radially locked position with respect to the first longitudinal axis of the main housing section, and g) wherein the proximal lever portion is further manipulatable about the pivot pin and against the bias of the spring to remove the lever pin from the first opening to thereby permit relative rotational movement of the handle grip connected to the handle head portion about the main housing section until the lever pin is aligned with the second one of the openings and then the proximal lever portion is manipulatable to cause the spring to bias the lever pin into registry with the second opening to thereby provide, with respect to the first longitudinal axis of the main housing section, the handle grip in a second radially locked position different than the first radially locked position.

19. The surgical reamer spindle of claim 18 wherein the lever resides at least partially within a recess in a sidewall of the handle head portion.

20. The surgical reamer spindle of claim 18 wherein there are four openings in the main housing section, the four openings being spaced at 90° intervals from each other in the plane aligned perpendicular to the first longitudinal axis.

21. The surgical reamer spindle of claim 18 wherein the locking mechanism comprises two levers pivotably secured to the handle head section, the levers being diametrically opposed to each other.

22. The surgical reamer spindle of claim 18 wherein the drive train comprises a drive shaft having a proximal drive shaft end spaced from a distal drive shaft end, the proximal drive shaft end being adaptable for releasable connection to a source of rotary motion.

23. The surgical reamer spindle of claim 18 wherein the handle assembly is composed of a polymeric material.

24. The surgical reamer spindle of claim 18 wherein the handle assembly is composed of a carbon fiber material.

25. The surgical reamer spindle of claim 18 wherein the reamer connector extending distally from the drive train comprises a bayonet-type connector.

26. The surgical reamer spindle of claim 18 wherein a proximal portion of the main housing section provided the at least two openings and supporting the handle assembly is cylindrical.

27. A surgical reamer spindle, which comprises:
a) a housing, comprising:
i) a main housing section extending along a first longitudinal axis;
ii) an intermediate housing section connected to a distal end of the main housing section; and
iii) a distal housing section connected to a distal end of the intermediate housing section,
iv) wherein the main housing section comprises a distal main housing portion connected to a cylindrical proximal main housing portion; and
v) at least two spaced apart openings in the cylindrical portion of the main housing section, the openings residing in a plane aligned perpendicular to the first longitudinal axis;

b) a drive train at least partially housed inside the housing, the drive train comprising:
i) a drive shaft having a proximal drive shaft end spaced from a distal drive shaft end, the proximal drive shaft end being adaptable for releasable connection to a source of rotary motion;
ii) a first, proximal U-joint rigidly connected to the distal, drive shaft end;
iii) a second U-joint pivotably connected to the first U-joint;
iv) an intermediary rod residing in the intermediate housing section and comprising a proximal rod end rigidly connected to the second U-joint opposite the first U-joint, wherein the pivotably connected first and second U-joints reside at a transition of the main housing section to the intermediate housing section;
v) a third U-joint rigidly connected to a distal end of the intermediary rod;
vi) a fourth, distal U-joint pivotably connected to the third U-joint; and
vii) a bayonet-type reamer connector rigidly connected to the fourth U-joint opposite the third U-joint, wherein the pivotably connection third and fourth U-joints reside at a transition of the intermediate housing section to the distal housing section;

c) a handle assembly comprising a handle head portion supporting a handle grip, wherein the handle head portion defines a throughbore that receives the main housing section in a radially rotatable relationship with respect to the first longitudinal axis;

d) a locking mechanism supported by the handle head portion, the locking mechanism comprising:
i) a lever pivotably supported by a pivot pin secured to the handle head portion, wherein the lever extends along a second longitudinal axis from a proximal lever portion to a distal lever portion, and wherein the second longitudinal axis is spaced from the first longitudinal axis of the main housing section;
ii) a lever pin at the distal lever portion, the lever pin extending inwardly toward the first longitudinal axis; and
iii) a spring positioned between the handle head portion and the proximal lever portion, e) wherein the proximal lever portion is pivotably manipulatable about the pivot pin and against a bias of the spring to register the lever pin in a first one of the at least two openings in the main housing section to thereby provide the handle grip supported by the handle head portion in a first radially locked position with respect to the first longitudinal axis of the main housing section, and f) wherein the proximal lever portion is further manipulatable about the pivot pin and against the bias of the spring to remove the lever pin from the first opening to thereby permit relative rotational movement of the handle grip connected to the handle head portion about the main housing section until the lever pin is aligned with the second one of the openings and then the proximal lever portion is manipulatable to cause the spring to bias the lever pin into registry with the second opening to thereby provide, with respect to the first longitudinal axis of the main housing section, the handle grip in a second radially locked position different than the first radially locked position.

28. The surgical reamer spindle of claim 27 wherein there are four openings in the cylindrical portion of the main housing section, the four openings being spaced at 90° intervals from each other in the plane aligned perpendicular to the first longitudinal axis and wherein the locking mechanism comprises two levers pivotably secured to the handle head section, the levers being diametrically opposed to each other.

29. The surgical reamer spindle of claim 27 wherein the handle assembly is at least partially composed of a carbon fiber material.

30. The surgical reamer spindle of claim 27 wherein the intermediate housing section extends along a third longitudinal axis that is at an intermediate housing angle ranging from 20° to 40° with respect to the first longitudinal axis so that the main housing section is offset from the distal neck section by an offset distance that ranges from 2 cm to about 5 cm, the offset distance defined as the distance between the first longitudinal axis extending along the main housing section and a fourth longitudinal axis extending along the distal neck section.

* * * * *

UNITED STATES PATENT AND TRADEMARK OFFICE
CERTIFICATE OF CORRECTION

PATENT NO. : 9,078,672 B1  
APPLICATION NO. : 13/290202  
DATED : July 14, 2015  
INVENTOR(S) : Yann Rosse Page 1 of 1

It is certified that error appears in the above-identified patent and that said Letters Patent is hereby corrected as shown below:

Title Page, Item 22, after "(22) Filed: Nov. 7, 2011" insert on the next line --Related U.S. Application Data-- and, on the next line, insert --Provisional application No. 61/410,418, filed on Nov. 5, 2010--

Signed and Sealed this  
Twelfth Day of July, 2016

Michelle K. Lee  
*Director of the United States Patent and Trademark Office*